United States Patent [19]

Dorman et al.

[11] Patent Number: 5,007,930

[45] Date of Patent: Apr. 16, 1991

[54] COMPOSITES OF UNSINTERED CALCIUM PHOSPHATES AND SYNTHETIC BIODEGRADABLE POLYMERS USEFUL AS HARD TISSUE PROSTHETICS

[75] Inventors: Linneaus C. Dorman, Midland, Mich.; Paul A. Meyers, Dublin, Calif.

[73] Assignee: The Dow Chemical Company, Midland, Mich.

[21] Appl. No.: 563,881

[22] Filed: Aug. 6, 1990

Related U.S. Application Data

[60] Continuation of Ser. No. 357,515, May 26, 1989, abandoned, which is a division of Ser. No. 56,496, Jun. 1, 1987, Pat. No. 4,842,604, which is a continuation of Ser. No. 914,419, Oct. 2, 1986, Pat. No. 4,698,375, which is a division of Ser. No. 702,998, Feb. 19, 1985, Pat. No. 4,636,526.

[51] Int. Cl.$^5$ ................................................. A61F 2/28
[52] U.S. Cl. ........................................ 623/16; 623/66; 427/2; 433/212.1
[58] Field of Search ................. 623/16, 66; 433/201.1, 433/202.1, 212.1; 427/2

[56] References Cited

U.S. PATENT DOCUMENTS 4,192,021  3/1980  Deibig et al. ......................... 623/16
4,373,217  2/1983  Draenert .............................. 623/16

Primary Examiner—Alan W. Cannon

[57] ABSTRACT

A process for the prosthetic supplementation or replacement of hard tissue. In the process an anatomically-shaped form is molded by or a prosthetic device is coated with a composite material containing unsintered calcium phosphate biomaterial, a synthetic biodegradable polymer, and optionally, a pore-forming agent.

9 Claims, No Drawings

COMPOSITES OF UNSINTERED CALCIUM PHOSPHATES AND SYNTHETIC BIODEGRADABLE POLYMERS USEFUL AS HARD TISSUE PROSTHETICS

CROSS-REFERENCE TO RELATED APPLICATION

This is a continuation of application Ser. No. 357,515 filed May 26, 1989, now abandoned, which is a division of application Ser. No. 056,496, filed Jun. 1, 1987, now U.S. Pat. No. 4,842,604, which is a continuation of Ser. No. 914,419 filed Oct. 2, 1986, now U.S. Pat. No. 4,698,375 which is a division of Ser. No. 702,998 filed Feb. 19, 1985, now U.S. Pat. No. 4,636,526.

FIELD OF THE INVENTION

The present invention relates to composite materials comprising synthetic biodegradable polymers and unsintered calcium phosphate biomaterials and processes for the preparation and use thereof. Said composite materials are useful as hard tissue prosthetics such as bone prosthetics.

BACKGROUND OF THE INVENTION

Calcium phosphates are known as physiologically acceptable biomaterials potentially useful as hard tissue prosthetics. The most widely studied of these are hydroxyapatite and tricalcium phosphate. When these materials are shaped and made porous they can be used alone or as a supplement or extender with bone for hard tissue prosthetics. Under appropriate conditions and with an appropriate form of calcium phosphate, the calcium phosphate is resorbed and new bone growth results. Porositizing the calcium phosphate results in increased surface area so that more calcium phosphate will be exposed to the body fluids facilitating resorption and growth of new bone tissue. Excellent control of the type and size of pores formed can be achieved by compaction of calcium phosphate powders containing naphthalene followed by removal of the naphthalene by leaching or sublimation. Hydrothermal exchange of marine coral structures (i.e., calcium carbonate for calcium phosphate), and decomposition of hydrogen peroxide have also been employed to generate pore filled structures.

The dense or "green" forms of the calcium phosphate implant materials have mechanical properties equal to or exceeding that of natural bone, but their respective porous forms do not, thus severely limiting their usefulness as hard tissue prosthetics.

It is known that certain natural and synthetic polymers can be used alone or in conjunction with other materials for bone prostheses or other implantable devices. Natural polymers include collagen (U.S. Pat. No. 4,192,021) and gelatin (German Patent No. 2,812,696). Synthetic polymers include polyacrylates, poly(methylmethacrylate), polyethylene, polysulfones, polyamides, polyesters, polytetrafluoroethylene, and polycarbonates (Great Britain Patent Application No. 2,031,450A); polyacetates and polyglycolates (U.S. Pat. No. 4,192,021); epoxides, polyacrylamide, polypropylene, polyurethanes, polyacetals, silicone resins, and furan resins (U.S. Pat. No. 4,222,128); polyvinyl pyrrolidone, polyvinyl alcohol (U.S. Pat. No. 4,263,185); and a cross-linked pentapeptide (U.S. Pat. No. 4,187,852). The natural polymers and some of the synthetic polymers are resorbable, i.e., biodegradable.

The art also teaches that nontoxic water soluble substances such as sodium chloride can be incorporated into a mixture of powdered acrylic polymer, liquid monomer, and other ingredients in a mold and the mixture polymerized to produce a shaped composite. The composite can then be made porous by leaching the sodium chloride with water (U.S. Pat. No. 4,199,864).

The various polymer-calcium phosphate composites are prepared in a number of ways including blending calcium phosphates with polymeric binder and subsequent molding (Great Britain Patent No. 1,593,288); impregnation of sintered, porous calcium phosphate with polymers under vacuum (Great Britain Patent No. 1,593,288); impregnation of a porous calcium phosphate body with the melt or solution of prepolymers and solidifying the polymers by further polymerization or curing in the pores or by evaporation of the solvent (U.S. Pat. No. 4,192,021); impregnation of a porous calcium phosphate body with a very reactive monomer like an α-cyanoacrylate or monomer and catalyst and polymerizing by heating (U.S. Pat. No. 4,192,021); compression molding of an intimately blended, finely powdered mixture of polymer and calcium phosphate (U.S. Pat. No. 4,192,021); and embedding calcium phosphate particles into resins where the calcium phosphate particles have previously been coated with a resin-affinic material to ensure good bonding to the resin, or copolymerizing precoated particles with the resin monomers (German Patent No. 2,620,907).

Calcium phosphate-polymer composite materials can also be used in conjunction with metallic or plastic prosthetics to facilitate adhesion and bone growth around the prosthetic (German Patent No. 2,905,647). The composite can also be applied as a coating, for example, to an anodized titanium/aluminum/vanadium alloy hip prosthetic (Great Britain Patent No. 1,593,288). The essential element in anchoring prosthetic devices appears to be the induction of new bone growth around the device by assuring that contact with the surrounding tissue is through a sheath of, or a surface laden with, bioactive calcium phosphate.

It is desired to have a composite material which is gradually absorbed by the host and is simultaneously replaced with bone tissue without any undesirable side effects such as extensive inflammation or extensive formation of connective tissue. It is also desirable to have a composite material based on calcium phosphates which has improved mechanical properties for use as hard tissue prosthetics over calcium phosphates alone. The prior art teaches composites which are comprised of certain polymers and certain calcium phosphates (U.S. Pat. No. 4,192,021); however, the calcium phosphates in composites of this type are taught as requiring a sintering step.

SUMMARY OF THE INVENTION

We have surprisingly found that the calcium phosphates in composites of synthetic biodegradable polymers and calcium phosphates do not require a sintering step in order for the composites to have the desirable properties described herein. The elimination of the need for sintering the calcium phosphates in the composites of the present invention is a significant improvement over the teachings in the prior art. Sintering involves heating at high temperatures, such as 1000° C. to 1300° C., which requires substantial levels of energy. Obviating the need for sintering therefore results in reduced energy consumption. In addition, elimination of a sintering step results in a savings of time. Therefore, the composites of the present invention can be prepared at reduced cost.

The present invention is directed to a composition of matter comprising an optionally porositized composite material of a synthetic biodegradable polymer and an unsintered calcium phosphate biomaterial. Especially preferred synthetic biodegradable polymers are α-amino acid polymers. A compatible, pore-forming agent such as a water-soluble polymer or water-soluble inert material may be blended with the composite materials of the present invention to form a dense, shaped comixture which may be made porous by leaching the water-soluble polymer or water-soluble inert material with water.

The composite materials disclosed herein may be used in a variety of applications such as, for example, hard tissue prosthetics for dental or orthopedic appliances or other applications where one skilled in the art would envision the use of physiologically acceptable and/or resorbable materials such as those described herein.

DETAILED DESCRIPTION OF THE INVENTION

The object of this invention is to provide a material which is gradually absorbed by the body and is simultaneously replaced with bone tissue. This invention relates to optionally porositized composites of unsintered calcium phosphates and polymers. The polymers in the composites of this invention are biocompatible synthetic polymers which are biodegradable. The composites of this invention have desirable mechanical and bioabsorption properties.

Suitable polymers for use in the composites of this invention can be made by the polymerization of monomers such as lactic acid, glycolic acid, hydroxybutyrate, amino acids, and the like. Examples of preferred polymers are polyesters of lactic acid, polyesters of glycolic acid, and polyhydroxybutyrate. Most preferred are polymers of α-amino acids. For the purpose of this invention, the term "synthetic biodegradable polymer" includes copolymers which are the polymerization product of at least two of the hereinabove described monomers and further includes mixtures of the hereinabove described polymers.

The α-amino acids utilized in the preparation of the preferred composite materials of the present invention may be any of the common, naturally occurring or synthetic α-amino acids. Preferred are those α-amino acids capable of undergoing polymerization through the corresponding reactive α-amino acid N-carboxyanhydride monomer (for convenience, hereinafter referred to as α-amino acid NCA).

Examples of the α-amino acids which can be used for preparation of the preferred composites include compounds such as aspartic acid, glutamic acid, lysine, arginine, alanine, valine, leucine, serine and the like. The α-amino acids used herein may be present in the D or L configuration or in the D,L configuration. Preferred are those α-amino acids exhibiting the L configuration.

It is necessary to insure that during the α-amino acid NCA polymerization no side chain reactions or interactions between amino and carboxyl functions of different amino acids occur. Such situations may be prevented by carrying out the reaction in such a way as to avoid said interactions or by using α-amino acids wherein protecting groups have been added to the side chain, amino and/or carboxyl functions. Amino acids having such protected functionalities are readily prepared by known techniques or are commercially available. See for example, the following publications *Solid Phase Peptide Synthesis*, J. Stewart and J. Young, W. H. Freeman & Co., San Francisco, 1969; *Synthetic Peptides*, G. Pettit, Vol. 1 (1970) and Vol. 2 (1971), Von Nostrand Reinhold Co., New York; and *The Peptides, Analysis, Synthesis, Biology*, E. Gross and J. Meienhofer, Academic Press, New York, 1979.

Of the α-amino acids which may be used in the present invention, glutamic acid is preferred. Glutamic acid may be polymerized by known techniques without the addition of the above-described protecting groups, or derivatives of glutamic acid may be used. Especially preferred for use herein are the γ-ester derivatives of glutamic acid of the formula:

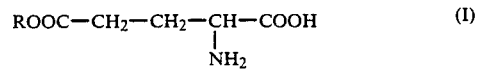

wherein R represents alkyl or aralkyl. As used herein, the term "alkyl" refers to aliphatic, straight or branched chain radicals of from about 1 to about 10 carbon atoms or cyclic aliphatic radicals of from about 3 to about 8 carbon atoms; "aralkyl" refers to radicals such as, for example, phenylethyl, benzyl, ring-substituted benzyl and the like. Most particularly preferred for use herein are those compounds of formula I wherein R is methyl or benzyl.

The α-amino acid NCA referred to above is prepared by the reaction of the desired α-amino acid with phosgene via procedures known to the art. See, for example, U.S. Pat. No. 3,658,831, and Fuller et al., "A Procedure for the Facile Synthesis of Amino-Acid N-Carboxyanhydrides" (*Biopolymers*, Vol. 15, p. 1869, 1976) which are incorporated herein by reference. For purposes of illustration, the N-carboxyanhydride of a compound of Formula I is prepared by the following reaction sequence (where R is as defined for Formula I):

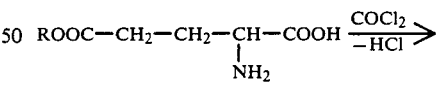

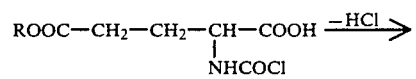

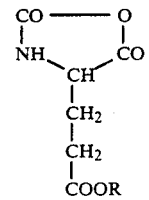

The α-amino acid NCA is then readily polymerized into the α-amino acid polymer as represented by the following:

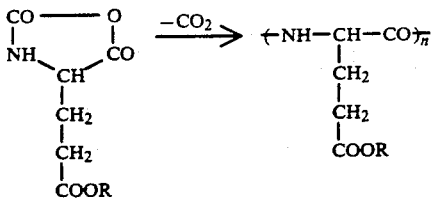

wherein R is as defined for formula I and n is a positive integer. The other α-amino acid polymers alluded to herein may be prepared in a manner analogous to the above-described reactions; the use of compounds of Formula I is merely illustrative. Further, one skilled in the art will appreciate that α-amino acid polymers may be prepared by techniques other than as described herein (i.e., by methods other than polymerization of an α-amino acid NCA monomer) such as by the use of active esters or triphenylphosphite with imidazole and the like.

In preparing the composites of this invention, the synthetic biodegradable polymer can be pre-polymerized and mixed with powdered unsintered calcium phosphate or the composite can be prepared by impregnating pre-formed unsintered calcium phosphate with monomer, prepolymer or polymer followed by polymerization if necessary. The most preferred method of preparing the composites of this invention is in situ polymerization of monomer in the presence of the powdered unsintered calcium phosphate.

The calcium phosphates of the composites of this invention may be one or more unsintered calcium phosphates such as, for example, calcium phosphate tribasic ($Ca_{10}(OH)_2(PO_4)_6$) also known as hydroxyapatite or simply apatite; unsintered tricalcium phosphate ($Ca_3(PO_4)_2$); or various unsintered calcium pyrophosphates. The composite materials may contain from about 25 to about 75 percent by weight, preferably from about 40 to about 60 percent by weight, of one or more unsintered calcium phosphate biomaterials, said biomaterials preferably being unsintered hydroxyapatite, unsintered tricalcium phosphate or mixtures thereof.

Optionally, and preferably, the composite material described herein may be made porous in order to facilitate tissue ingrowth, a phenomenon where tissue such as bone and tendon continue to grow after the prosthetic device is in place and occupy apertures adjacent to the tissue. The tissue ingrowth provides a means by which a prosthetic device may be secured, thereby providing mechanical stabilization of the implant.

The preferred composites containing α-amino acid polymers prepared as described herein are permeable to oxygen and water and are biodegradable, presumably due to the presence of peptide bonds in the α-amino acid polymer matrix making the substances protein-like. As resorption of the unsintered calcium phosphate biomaterial occurs followed by a slow degradation of the α-amino acid polymer matrix, further porositization results, thereby facilitating tissue ingrowth. For example, as the unsintered calcium phosphate biomaterial is resorbed and the α-amino acid polymer matrix slowly degrades, new, natural, self-supporting hard tissue develops.

Further, in the composites containing α-amino acid polymers, various combinations of α-amino acids may be polymerized with one or more calcium phosphate biomaterials. By so doing, the characteristics of the resulting composite material may be modified so as to vary the rate of resorption of the inorganic filler and/or the rate of degradation of the polymer matrix, thus allowing one skilled in the art to design a given composite for a highly specific application.

The composite materials of the present invention may be ground to fine, free-flowing powders making them convenient to use. The free-flowing powders can be readily molded to virtually any shape, preferably a shape capable of anatomical use as a prosthetic device. Such anatomically-shaped forms may then be surgically implanted into animals including humans in need of such prostheses thereby providing supplementation or replacement of hard tissue. It is further contemplated that the composite materials described herein may be used in conjunction with conventional prosthetic devices known to the art. (See, for example, publications such as U.S. Pat. Nos. 4,362,681, 4,351,069 and 3,986,212, which describe various conventional prostheses.) For instance, in total hip joint replacements, it would be possible to mold one or more of the composite materials of the present invention about the metal stem of the prosthetic which, when implanted into the femur, would present a compatible surface for new bone growth while being sufficiently strong to support the metal prosthesis. This and other applications of the technology disclosed herein will be readily appreciated by one skilled in the art.

In the in situ preparation of the preferred composite materials containing α-amino acid polymers the desired α-amino acid (having, if necessary, protected side chain, amino and/or carboxyl functionalities) is treated with phosgene to form the reactive α-amino acid NCA monomer. While various phosgenation processes are known to the art, it is preferable that a process substantially the same as that described in U.S. Pat. No. 3,658,831 be utilized in order to prepare an α-amino acid NCA of the desired purity. It is important to obtain very highly pure α-amino acid NCA in order to prepare α-amino acid polymers having a high degree of polymerization and high quality. The α-amino acid NCA thus obtained is then admixed with one or more of the desired unsintered calcium phosphate biomaterials in a suitable inert organic solvent such as chloroform, dioxane, tetrahydrofuran (THF), methylene chloride or mixtures thereof. Preferably, the inert organic solvent utilized is dioxane, THF or mixtures thereof. For in situ polymerization the calcium phosphate biomaterial must be in a powdered or particulate form. Typically the calcium phosphate particles are between about 0.05 micrometers ($\mu m$) and 10 $\mu m$ in diameter and preferably about 1 $\mu m$ in diameter. As noted earlier, the composite material may be composed of from about 25 to about 75 percent by weight, preferably from about 40 to about 60 percent by weight of one or more unsintered calcium phosphate biomaterials, preferably unsintered hydroxyapatite, unsintered tricalcium phosphate, or mixtures thereof. Correspondingly, the α-amino acid polymer represents from about 75 to about 25 percent by weight, preferably from about 60 to about 40 percent by weight of the composite formed. Typically, the α-amino acid NCA and calcium phosphate biomaterial mixture is stirred for a period of time sufficient to effect formation of the desired composite material (usually from about 2 to about 12 days) at a temperature of from about 18° to about 30° C. It is preferred that the mixture be stirred for about 3 to about 6 days at ambient temperature and pressure.

Notably, the above-described in situ polymerization of the α-amino acid NCA and calcium phosphate biomaterial proceeds spontaneously at ambient temperature without the need for initiators. Further, it is unnecessary to use a solvent system in which both the α-amino acid NCA monomer and resultant α-amino acid polymer are soluble. For example, poly(γ-methyl)-L-glutamate is insoluble in dioxane or THF, two solvents frequently used for the polymerization. The in situ polymerization process of the preferred composite materials results in an intimate bonding between the resulting α-amino acid polymer and unsintered calcium phosphate biomaterial, not merely a mixture of said components.

Once the preferred composite material has been prepared by the in situ method, it can be molded by techniques well-known to the art to virtually any desired shape while maintaining the complete integrity of the composite material.

Porositization of the composite materials described herein may be attained by intimately blending the powdered composite with a compatible, pore-forming agent. Such pore-forming agents include water-soluble polymers (such as poly(2-ethyl-2-oxazoline), hereinafter referred to as PEOX; polyvinyl pyrrolidone; polyvinyl alcohol; or methylcellulose) and/or water soluble inert materials (such as sodium chloride or potassium chloride). The mixture obtained may then be molded to the desired configuration, followed by a leaching of the compatible, pore-forming agent with water. Said leaching typically occurs satisfactorily in a time from about 2 to about 21 days. Preferably, for the porositization process, PEOX or sodium chloride is utilized as the pore-forming agent in a range of from about 5 to about 30 percent by weight, preferably in a range of from about 10 to about 20 percent by weight (based on the total weight of the composite plus pore-forming agent). Sodium chloride is particularly preferred as a pore-forming agent and is most particularly preferred when used in a range of from about 10 to about 20 percent by weight (based on the total weight of the composite plus pore-forming agent).

The following examples are provided as a means of illustrating the present invention and are not to be construed as a limitation thereon.

EXAMPLE 1

γ-Benzyl L-Glutamate 1416 grams (g) of L-glutamic acid, 1560 g of 60% sulfuric acid and 1152 g of benzyl alcohol were placed in a 12 liter round bottom flask equipped with a distillation head. The mixture was heated to 70° C. and stirred for 45 minutes. Upon cooling, the resulting solution was stirred and was subjected to a reduced pressure. When the vacuum had stabilized at about 100 millimeters (mm) the reaction temperature was again raised to 70° C. and water was distilled off for about 4.5 hours. Upon standing overnight, the reaction mixture became viscous and was slowly added to a stirred mixture of 1613 g of sodium bicarbonate, 1.2 kilograms (kg) of ice and 12 liters of water. A precipitate formed which was collected by filtration and subsequently washed with about 8 liters of carbon dioxide-free water and 8 liters of acetone and subsequently air-dried. The precipitate was triturated with 2 liters of ether and dried, yielding 1044 g of the desired γ-benzyl L-glutamate, melting point (m.p.) 156°–157° C. Thin layer chromatography detected the presence of unreacted glutamic acid in the crude product. The crude product was recrystallized from 12.5 liters of hot water and filtered through a plug of glass wool suspended in the neck of a heated glass funnel. After cooling, and overnight refrigeration, the recrystallized product was collected, and washed with 2 liters of cold water, then 2 liters of THF. The product was air dried overnight and then dried in vacuo at room temperature for three hours. 693 g of γ-benzyl L-glutamate was recovered as white, shiny plates, m.p. 156.5°–157° C.

Following a procedure substantially the same as that described in Example 1, the following two compounds were prepared using the requisite starting materials.

EXAMPLE 2

γ-Benzyl D,L-Glutamate, m.p. 145°–146° C.

EXAMPLE 3

γ-Hexyl L-Glutamate, m.p. 162.5°–163° C.

EXAMPLE 4

γ-Methyl L-Glutamate

A cold solution of 300 ml of acetyl chloride was slowly added to a flask containing 3 liters of methanol. To this mixture was added 442 g of L-glutamic acid. The flask was stoppered and shaken for several minutes to effect solution. The flask was then allowed to stand at room temperature with intermittent shaking for 24 hours. 300 ml of pyridine was added causing a precipitate to form. Upon standing for an additional 48 hours, the precipitate was collected on sintered glass and washed with two 600 ml portions of ethanol and a 250 ml portion of ether. The precipitate was dried in vacuo at room temperature for 3 hours and then in a vacuum desiccator over Drierite ® for 5 hours. Pyridine vapors were still perceptible from the precipitate which was further triturated with ether and dried again yielding 201.5 g of the desired γ-methyl L-glutamate as white, shiny plates, m.p. 168°–169° C.

EXAMPLE 5

γ-Methyl D,L-Glutamate

γ-Methyl D,L-glutamate was prepared by substantially the same method as described in Example 4, yielding white, powder-like crystals, m.p. 166°–166.3° C.

EXAMPLE 6

γ-Benzyl L-Glutamate N-Carboxyanhydride 92.7 g of γ-benzyl L-glutamate and 840 ml of THF were mixed and heated in a 3 liter reaction flask. Nitrogen and phosgene were bubbled in and the reaction temperature was maintained between 45°–50° C. until complete solution of the starting material had occurred (about 2 hours). Heating and phosgene flow were then stopped, but stirring and nitrogen flow were continued as the reaction mixture cooled slowly to 30° C. (approximately 45 minutes). The reaction flask was carefully removed from the phosgenation apparatus and stoppered. The reaction mixture was then concentrated in vacuo to about 250 ml with the aid of a rotary evaporator (maximum bath temperature about 35° C.). The residual concentrate was transferred to a dry flask and diluted carefully with an equal volume of hexane and seeded. After allowing crystallization to proceed at room temperature for about an hour, the reaction mixture was further diluted with about 500 ml of hexane and was maintained at −30° C. for about 8-10 hours. After warming to room temperature the product was collected on a sintered glass funnel, care being taken to minimize contact with atmospheric moisture. The product was rinsed with a mixture of THF-hexane (1:3) and then hexane, covered with a filter paper and dried in a vacuum desiccator over Drierite ®. 92.6 g of the desired γ-benzyl L-glutamate N-carboxyanhydride was recovered as white crystals, m.p. 95°-96° C.

EXAMPLE 7

γ-Methyl L-Glutamate N-Carboxyanhydride 100 g of γ-methyl L-glutamate and 600 ml of THF were placed in a 2 liter flask under nitrogen. The ensuing phosgenation reaction was carried out as described in Example 6, above. The reaction temperature was maintained between 44°-49° C. for about 3 hours. Heating and phosgene addition were discontinued and stirring of the reaction mixture under nitrogen continued for about 1 hour before working up as described previously. 93.9 g of the desired γ-methyl L-glutamate N-carboxyanhydride was recovered as dense, white crystals, m.p. 97.5°-99° C.

EXAMPLE 8

Hydroxyapatite-Poly(γ-Methyl-L-Glutamate) Composite 5.0 g of γ-methyl L-glutamate N-carboxyanhydride was added to 50 ml of a mixture of dioxane-THF (3:1). Upon solubilization, 5.9 g of dry unsintered calcium phosphate tribasic (i.e., hydroxyapatite) was added and the mixture was stirred at room temperature for seven days. The mixture was then poured with stirring into 300 ml of methanol and the product composite was collected by filtration, washed with methanol and dried in vacuo at 80° C. for 6 hours. 9.58 g of a soft, white, homogeneous solid was obtained and subsequently identified as hydroxyapatite-poly(γ-methyl L-glutamate) composite consisting of 61% (by weight) hydroxyapatite. This composite material was easily ground to a fine powder.

EXAMPLE 9

Hydroxyapatite-Poly(γ-Methyl L-Glutamate) Composite

Following a procedure substantially the same as that described in Example 8, 65.2 g of γ-methyl L-glutamate N-carboxyanhydride, 50 g of unsintered hydroxyapatite and 675 ml of a mixture of dioxane-THF (3:1) were stirred continuously for 5 days. Two liters of methanol were then added to the mixture and the desired composite material was recovered as described in Example 8. 98 g of the desired hydroxyapatite-poly(γ-methyl L-glutamate) composite material consisting of 50% (by weight) hydroxyapatite was subsequently recovered.

EXAMPLE 10

Hydroxyapatite-Poly(γ-Benzyl L-Glutamate) Composite 72.6 g of γ-benzyl L-glutamate N-carboxyanhydride, 40 g of unsintered hydroxyapatite, and 700 ml of a mixture of dioxane-THF (3:1) were continuously stirred for four days. The reaction mixture was then poured with stirring into 2500 ml of ethanol and collected by filtration. The residue from the filtration was washed with ethanol, air dried and then dried in vacuo at 60°-70° C. for six hours. 98 g of the desired hydroxyapatite-poly(γ-benzyl L-glutamate) composite material (60 percent by weight hydroxyapatite) was obtained as a white, short fiber-like solid.

EXAMPLE 11

A hydroxyapatite-poly(γ-benzyl L-glutamate) composite was ground and sieved through a 20-mesh screen. PEOX (molecular weight about 200,000) was ground and sieved through a 35-mesh screen. Enough PEOX was added to the ground composite to constitute about 15 percent by weight of the total mixture (i.e., composite plus PEOX) and the mixture was blended by tumbling on a roller for 2 hours. This mixture was then compression molded in nickel plated stainless steel pressurized dies held in a ram press under a 2.5 ton load at 160° C. One die was cylindrical in shape and produced a pressure of about 25,500 pounds per square inch (psi) at the composite surface. Another die was dogbone shaped, producing a pressure of about 2600 psi at the composite surface. Molding time was 20 minutes, with about 10 minutes additional time being allowed for the preheated press and die to approach the desired molding temperature. About 3-3.5 g of the composite-PEOX mixture was used to produce a molded, 0.5 inch disc in the cylindrical die. Similarly, about 7-7.5 g of the composite-PEOX mixture was used to produce 0.125 inch thick bars in the dogbone shaped die. The molded products were white, smooth, homogeneous objects.

EXAMPLE 12

The same procedure used in Example 11 was repeated utilizing a hydroxyapatite-poly(γ-methyl L-glutamate) composite and PEOX mixture. The mixture was molded in the dies described above under 2.5 ton load at 220° C. The molded products were white, smooth, homogeneous objects.

EXAMPLE 13

The same procedures utilized in Examples 11 and 12 were again repeated using sodium chloride in place of PEOX as the pore-forming agent. Again, the resulting molded products were white, smooth, homogeneous objects.

EXAMPLE 14

In order to illustrate the porositization technique, a 2.934 g molded disc containing 87 percent hydroxyapatite-poly(γ-methyl L-glutamate) composite material (50 percent by weight of each constituent) and 13 percent PEOX blended therein was placed in 20 ml of water in a closed container for a total of six days (the water was changed after four days). The disc was removed and dried by blotting with absorbent paper and then further dried in an oven at 60° C. 0.325 g of weight was lost representing 85.3 percent of the available PEOX in the molded disc. Microscopy of a section of the porositized product showed pore sizes of 10-25 microns.

Utilizing the above procedure, a molded disc containing 85 percent hydroxyapatite-poly(γ-methyl L-glutamate) composite (50 percent by weight of each component) and 15 percent by weight sodium chloride blended therein was placed in water in a closed container (48 percent of the available sodium chloride was removed). Microscopy of a section of the disc showed varied pore sizes, some in excess of 100 microns.

Utilizing procedures described herein, additional composite materials set forth in Table 1 were prepared.

Table 2 describes the mechanical properties of various molded composite materials of the present invention.

TABLE 1

| Example No. | Composite Material Polymer[a] | Calcium Phosphate Biomaterial[b] (Weight %) | Porositization Mode Agent (Amount)[c] | Amount Removed[d] |
|---|---|---|---|---|
| 15 | PGMLG | HA (50) | None | — |
| 16 | PGMLG | HA (50) | None | — |
| 17 | PGMLG | HA (50) | PEOX (15) | 80 |
| 18 | PGMLG | HA (50) | PEOX (15) | 122[e] |
| 19 | PGMLG | HA (50) | NaCl (15) | 48 |
| 20 | PGBLG | HA (40) | None | — |
| 21 | PGBLG | HA (40) | None | — |
| 22 | PGBLG | HA (40) | PEOX (15) | 29 |
| 23 | PGBLG | HA (40) | PEOX (15) | 59 |
| 24 | PGMLG | HA (50) | NaCl (10) | 55 |
| 25 | PGMLG | HA (50) | NaCl (20) | 40 |
| 26 | PGMLG | HA (41) | NaCl (15) | 46 |
| 27 | PGMLG | HA (75) | NaCl (15) | 78 |

[a]Abbreviations: PGMLG = poly(γ-methyl L-glutamate) PGBLG = poly(γ-benzyl L-glutamate)
[b]Abbreviations: HA = hydroxyapatite
[c]Weight percent of the porositizing agent based on the total weight of the composite material plus porositizing agent.
[d]Refers to the percent by weight of porositizing agent removed (based on the theoretical amount of porositizing agent available) by leaching with water.
[e]Result due to error in weighing.

TABLE 2
MECHANICAL PROPERTIES OF VARIOUS COMPOSITE MATERIALS

| Composite of Example No. | Vicat Heat Distortion | Compression Data Strength (psi) | Deformation (%) | Recovery[a] (%) | Modulus (psi × 10⁵) |
|---|---|---|---|---|---|
| 15 | — | 12,380 | 0.20 | — | 4.28 |
| 16 | 230° C. | — | — | — | — |
| 17 | — | 5,177 | — | — | — |
| 18 | 230° C. | — | — | — | — |
| 19 | — | 9,029 | 3.6 | 27.8 | 3.75 |
| 20 | — | 3,809 | 1.25 | 42.4 | 1.78 |
| 21 | 99° C. | — | — | — | — |
| 22 | — | 3,542 | — | — | — |
| 23 | 91° C. | — | — | — | — |
| 26 | — | 9,399 | 1.89 | 31.0 | 2.65 |
| 27 | — | 8,017 | 1.26 | 20.0 | 4.3 |

[a]After 24 hours.

EXAMPLE 28

Molded discs containing 85 percent hydroxyapatite-poly(γ-methyl L-glutamate) composite (50 percent by weight of each component) and 15 percent sodium chloride blended therein (hereafter referred to as the 15 percent NaCl composite discs) were porositized by the general techniques described herein. Similarly, molded discs containing 80 percent hydroxyapatite-poly(γ-methyl L-glutamate) composite (50 percent by weight of each component) and 20 percent sodium chloride blended therein (hereafter referred to as the 20 percent NaCl composite discs) were also prepared and porositized for evaluation in the study described below.

Small pieces of the above-described molded composites were cut from the larger discs with a diamond blade and subsequently autoclaved for sterilization. The sterilized pieces were then surgically implanted into rabbits in an incision in the paravertebral muscles of the lumbar region and in a hole drilled in the iliac crest. X-rays taken 6 and 12 weeks later of the rabbits implanted with the 15 percent NaCl composite discs showed no remarkable soft-tissue response in the lumbar paravertebral muscles indicating absence of a chronic inflammatory reaction. The bony implant sites exhibited healing and a regeneration of new bone incorporating the surgically implanted composite material. The animals were sacrificed at 14 weeks and the discs and surrounding musculature of the paravertebral implant were excised for microscopic evaluation. Likewise, iliac crest sections containing the implant sites were surgically removed, decalcified and were subsequently made into paraffin embedded sections. Upon examination, the discs showed a thin, fibrous encapsulation of from about 10 to about 50 microns evidencing only a minor foreign body response.

Animals implanted with the 20 percent NaCl composite discs showed a similar clinical history except that eight weeks after implantation there was no fibrous capsule formation around the implants and marrow was observed growing into the pores of the discs.

What is claimed is:

1. A process for the prosthetic supplementation or replacement of hard tissue which comprises coating a conventional prosthetic device with a composite material containing from about 25 to about 75 percent by weight of an unsintered calcium phosphate biomaterial and about 75 to about 25 percent by weight of synthetic biodegradable polymer.

2. The process of claim 1 wherein said synthetic biodegradable polymer is an α-amino acid polymer.

3. The process of claim 2 wherein said composite material also contains from about 5 to about 30 percent by weight of a pore-forming agent capable of porositization of the composite material, (said weight of the pore-forming agent being based on the total weight of the composite material plus pore-forming agent).

4. The process of claim 2 wherein said composite material also contains from about 10 to about 20 percent by weight of a pore-forming agent capable of porositization of the composite material, (said weight of the pore-forming agent being based on the total weight of the composite material plus pore-forming agent).

5. A process for the prosthetic supplementation or replacement of hard tissue which process comprises coating a conventional prosthetic device with a composite material containing from about 25 to about 75 percent by weight of an unsintered calcium phosphate biomaterial, wherein the unsintered calcium phosphate biomaterial is unsintered hydroxyapatite or unsintered tricalcium phosphate and about 75 to about 25 percent by weight of synthetic biodegradable polymer, and the biodegradable polymer is a glutamic acid-γ-ester polymer.

6. The process of claim 5 wherein the glutamic acid-γ-ester is glutamic acid-γ-methyl ester.

7. The process of claim 5 wherein the glutamic acid-γ-ester is glutamic acid-γ-benzyl ester.

8. The process of claim 6 wherein said composite material contains from about 40 to about 60 percent by weight of said unsintered calcium phosphate biomaterial.

9. The process of claim 7 wherein said composite material contains from about 40 to about 60 percent by weight of said unsintered calcium phosphate biomaterial.

* * * * *